(12) United States Patent
Gabbay

(10) Patent No.: US 6,599,318 B1
(45) Date of Patent: Jul. 29, 2003

(54) IMPLANTABLE SUPPORT APPARATUS AND METHOD OF USING SAME

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

(21) Appl. No.: 09/451,342

(22) Filed: Nov. 30, 1999

(51) Int. Cl.[7] .............................. A61F 2/00; A61B 17/04
(52) U.S. Cl. ....................... 623/11.11; 606/151; 600/37
(58) Field of Search ................................. 606/148, 149, 606/151, 144, 139; 600/37, 23.72; 623/11.11, 66

(56) References Cited

U.S. PATENT DOCUMENTS

| | | | |
|---|---|---|---|
| 2,587,966 A | | 3/1952 | Cleary |
| 5,275,578 A | | 1/1994 | Adams |
| 5,290,217 A | | 3/1994 | Campos |
| 5,330,488 A | | 7/1994 | Goldrath |
| 5,441,508 A | | 8/1995 | Gazielly et al. |
| 5,462,560 A | * | 10/1995 | Stevens ..................... 606/148 |
| 5,468,242 A | | 11/1995 | Reisberg |
| 5,649,937 A | * | 7/1997 | Bito et al. .................. 606/148 |

OTHER PUBLICATIONS

Product Brochure for Shelhigh No–React PERICARDIAL PATCH, (2pgs).

"Long–Term Outcome and Quality of Life After Modified Pubovaginal Sling for Intrinsic Sphincteric Deficiency", by Mohamed F. Hassouna and Gamal M. Ghoniem Urology, vol. 53, pp. 287–291, 1999.

"Use of the Fascial Sling for Neurogenic Incontinence: Lessons Learned", by Ross M. Decter, pp. 683–686, The Journal of Urology, vol. 150, pp. 683–686 Aug. 1993.

Instructions for Use, "In–Fast Bone Screw System for Transvaginal Cystourethropexy and Vaginal Sling Procedures", Influence Medical Technologies Ltd., 1997 (8pgs).

U.S. Gabbay patent application Ser. No. 09/388,416, filed Sep. 1, 1999.

* cited by examiner

Primary Examiner—David J. Isabella
(74) Attorney, Agent, or Firm—Tarolli, Sundheim, Covell & Tummino L.L.P.

(57) ABSTRACT

An implantable support apparatus includes a sheet of a flexible biocompatible material having apertures formed through end portions thereof to provide suture holes. A plurality of relatively larger apertures are formed through an intermediate portion of the sheet located between the end portions of the sheet to promote adhesion and improve integration of the apparatus into a patient's body. Threading mechanisms having elongated tubular projections are inserted into the apparatus at the end portions to facilitate threading sutures through such apertures.

10 Claims, 3 Drawing Sheets

IMPLANTABLE SUPPORT APPARATUS AND METHOD OF USING SAME

RELATED APPLICATIONS

This application is related to U.S. patent application Ser. No. 09/388,416, which was filed Sep. 1, 1999, now U.S. Pat. No. 6,355,065, and is entitled IMPLANTABLE SUPPORT APPARATUS AND METHOD OF USING SAME.

TECHNICAL FIELD

The present invention relates to an implantable support apparatus and to a method of using and to a method of making an implantable support apparatus.

BACKGROUND OF THE INVENTION

An implantable support, such as a sheet or patch of flexible material, is used to provide additional support to weakened or destabilized tissue of a patient. The implantable support is used to treat a variety of conditions, including, for example, closing a hernia and providing suburethral stabilization. The support may be formed of biological tissue or a synthetic material.

Some materials currently being used to manufacture such supports fail to attach adequately to surrounding tissue or experience undesirable deformation after implantation. Such conditions often require an additional surgical procedure and/or result in discomfort to the patient.

In one particular procedure, commonly known as a transvaginal or pubovaginal sling procedure, a patch or strip of biological tissue is used to provide suburethral stabilization for female patients experiencing bladder dysfunction, such as stress urinary incontinence. However, ends of the strip are friable and tend to weaken or rupture upon penetration by a relatively large needle. In addition, conventional biological strips are not easily integrated into the surrounding tissue due to their biocompatibility.

SUMMARY OF THE INVENTION

One aspect of the present invention provides an implantable support apparatus that includes a sheet of flexible biocompatible material having first and second end portions. A first pair of apertures extend through the sheet near the first end portion and a second pair of apertures extend through the sheet near the second end portion. First and second threading mechanisms are provided. Each of the threading mechanisms has a pair of tubular projections insertable into a selected pair of the apertures to facilitate threading of sutures through the first and second.pairs of apertures.

Another aspect of the present invention provides a method of using an implantable sheet of biocompatible material. The method includes providing an elongated sheet of flexible biocompatible material having first and second end portions. Apertures are formed through the sheet at locations near each of the first and second end portions. An elongated tubular projection is inserted into each of the apertures. Sutures are inserted through each of the tubular projections, which tubular projections are then removed so that the sutures remain in the apertures of the sheet. The sheet of material may be then connected to desired tissue using the sutures.

Yet another aspect of the present invention provides a method of making an implantable support apparatus. The method includes providing a sheet of flexible biocompatible material having first and second end portions. Apertures are formed through the sheet near each of the end portions. Elongated tubular projections are inserted through each of the first apertures so that threading of sutures through the apertures is facilitated.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EXEMPLARY EMBODIMENTS

Figure 1:
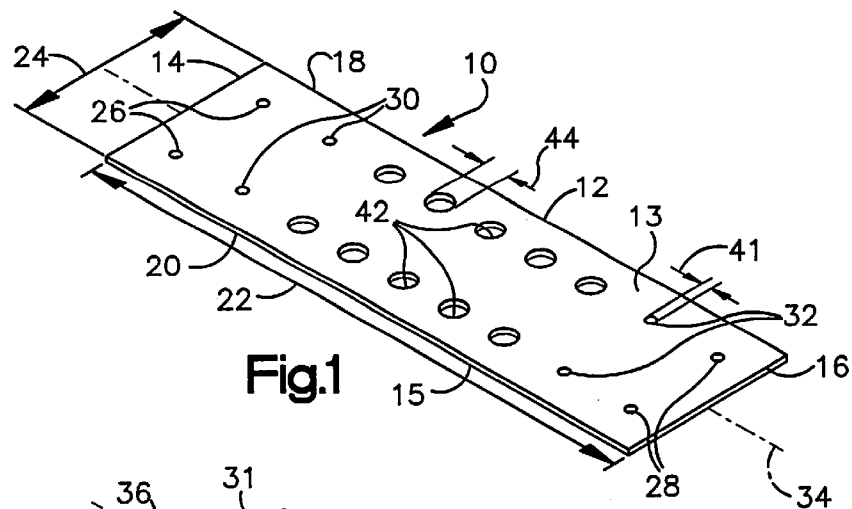
FIG. 1 is an isometric view of a support apparatus in accordance with a first embodiment of the present invention.
Figure 2:
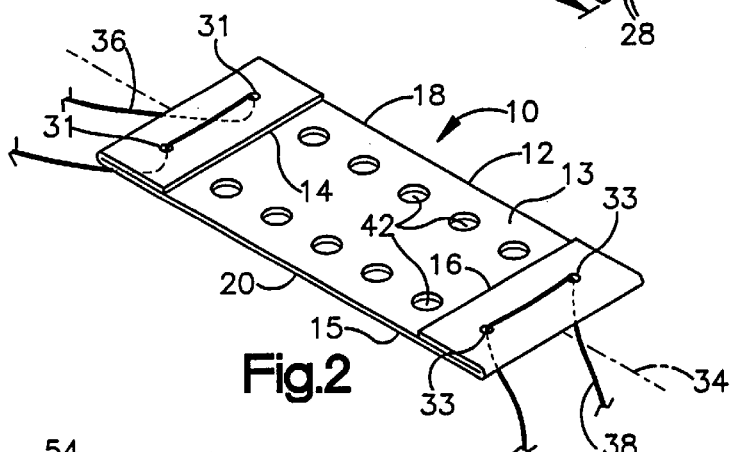
FIG. 2 is another view of the apparatus of FIG. 1 illustrating the end portions thereof in a folded condition.

FIGS. 1 and 2 illustrate a first embodiment of an implantable support apparatus 10 in accordance with the present invention. The apparatus 10 is in the form of a substantially flat strip or sheet 12 of a flexible, biocompatible material. The sheet 12 has opposed surfaces 13 and 15 which, for purposes of simplicity of explanation, are shown to be substantially planar in the views of FIGS. 1 and 2.

The sheet 12 may be made of a synthetic material or a biological material, such as human fascia lata (e.g., homografts) or treated pericardium from animals (e.g., heterografts). Preferably, the biological material is glutaraldehyde cross-linked pericardium which has been substantially detoxified and rinsed with heparin. By way of example, the treated biological tissue is a cytocompatible sheet of pericardium, such as the NO-REACT® Pericardial Patch or other tissue products commercially available from Shelhigh, Inc., of Millburn, N.J. Such pericardium may be bovine pericardium, porcine pericardium, or equine pericardium, although other types of treated biological tissue also could be used.

The sheet 12 includes end portions 14 and 16 that are spaced apart by elongated side edges 18 and 20. The side edges 18 and 20 extend a length of the sheet 12, indicated at 22. Similarly, the end portions 14 and 16 extend between the side edges 18 and 20 to define the width of the sheet 12, indicated at 24. The particular dimensions of the sheet 12 of material, including the width 24, length 22 and thickness thereof, vary depending upon the intended use of the apparatus 10.

For example, the apparatus 10 may be used for closure of a hernia (see FIG. 8) in which the length may approximate its width. The apparatus 10 also may be used to provide desired support in a suburethral stabilization procedure (see FIG. 7) in which its length will be greater than its width. Accordingly, the apparatus may be fabricated in a variety of sizes, such as, for example, 2×7 cm, 2×10 cm, 5×5 cm, 6×8 cm, 6×10 cm, 10×15 cm, and 10×20 cm.

As shown in FIG. 1, a plurality of apertures 26 and 289 extend from one surface 13 of the sheet 12 to other surface 15 near each of the respective end portions 14 and 16. Preferably, two pairs of apertures 26 and 30 are formed through the sheet 12 near one end portion 14 and two pairs of apertures 28 and 32 are formed through the sheet near the other end portion 16. It is also contemplated that other numbers of apertures may be formed through the respective end portions 14 and 16.

Each aperture of each respective apertures pair 26, 28, 30, 32 is preferably spaced the same distance from its adjacent end portion 14, 16. In this embodiment, the apertures 26 and 28 are located closer to their respective end portions 14 and 16 than are the other associated pairs of respective apertures 30 and 32. In particular, each of the apertures 26, 28 is configured to align substantially coaxially with an associated one of the respective apertures 30, 32 when the end portions are folded, as shown in FIG. 2. That is, each of the end portions 14, 16 may be folded on itself transverse to a long axis 34 of the sheet 12 and toward the opposed end portion 16, 14 to provide overlapping and engaging layers of the sheet 12 at the corresponding ends of the apparatus 10.

As shown in FIG. 2, the aligned pairs of apertures 26 and 30 form suture holes 31 and the other aligned pairs of apertures 28 and 32 form suture holes 33. The suture holes 31 and 33 extend substantially coaxially through the overlapping layers of the sheet 12 near their respective end portions 14 and 16. The overlapping layers of the sheet 12 at the folded ends increases the thickness of the apparatus 10 at the respective end portions. This reinforces the suture holes 31 and 33 and, in turn, helps prevent tearing and fraying when the apparatus 10 is implanted. Consequently, the longevity of the apparatus 10 also is improved.

The apertures 26, 28, 30, and 32 are dimensioned and configured for receiving a needle and/or a suture filament through the apertures. Accordingly, cross-sectional diameter of the apertures 26, 28, 30, and 32 may vary based on the desired size of sutures to be used during implantation of the apparatus 10. As shown in FIG. 2, sutures 36 and 38 are threaded through the respective suture holes 31 and 33 to secure the apparatus 10 to desired tissue of the patient such as to bone, muscle, or connective tissue. Preferably, each of the apertures 26, 28, 30, 32 has the same cross-sectional diameter, indicated at 41.

The apparatus 10 also includes a plurality of other apertures 42, which are larger than the apertures 26, 28, 30, and 32. The apertures 42 are formed through an intermediate portion of the sheet 12 at locations spaced from and located between each of the pairs of apertures 26–32 located near the end portions 14 and 16.

By way of example, the apertures 42 have cylindrical sidewall portions that extend axially between the surfaces 13 and 15. The axial length of the sidewall portions of each aperture 42, thus, is defined by the thickness of the sheet 12. As shown in FIG. 1, the cylindrical sidewall of each aperture 12 has a diameter 44 that is greater than the diameter 41 of the apertures 26, 28, 30, and 32 located at the end portions 14 and 16. For example, each of the apertures 42 has a diameter 44 ranging from about 2 mm to about 5 mm, and the diameter 41 of apertures 26, 28, 30, and 32 ranges from about 0.5 mm to about 2 mm.

While each of the apertures 26, 28, 30, 32, 42 is illustrated as a right, circular cylinder, each such aperture also could have another cross-sectional shape, such as a rectangular or polygonal cylinder or conical. In addition, while the apertures 42 are illustrated as being of uniform diameter, apertures having various diameters may be used on a single apparatus 10. The apertures 42 also could be randomly spaced along the intermediate portion of the strip 12 instead of discrete rows of apertures, as shown in the figures.

Figure 3:
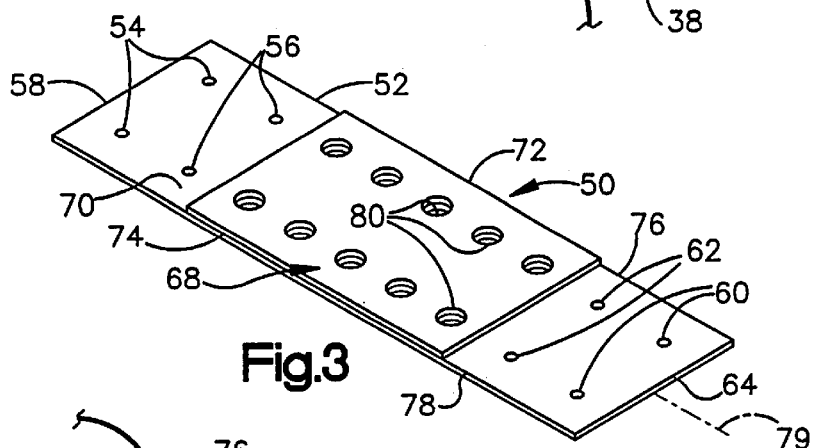
FIG. 3 is an isometric view of a support apparatus in accordance with a second embodiment of the present invention.
Figure 4:
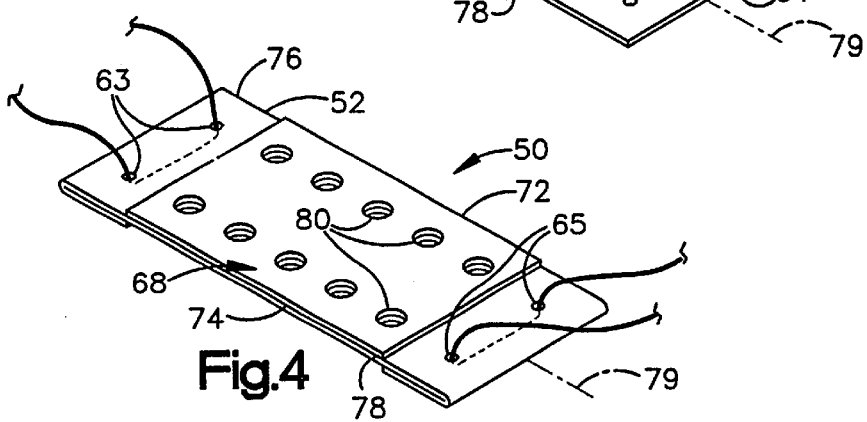
FIG. 4 is another view of the apparatus of FIG. 3, illustrating the end portions thereof in a folded condition.

FIGS. 3 and 4 illustrate another exemplary embodiment of an apparatus 50 in accordance with the present invention. The apparatus 50 includes an elongated sheet 52 of a flexible, biocompatible material that is substantially identical to the sheet 12 shown and described with respect to FIGS. 1 and 2.

Referring to FIG. 3, briefly stated, the sheet 52 has first and second pairs of apertures 54 and 56 formed through the sheet near one end portion 58 and third and fourth pairs of apertures 60 and 62 formed through the sheet near the other end portion 64. Corresponding ones of the apertures align with each other when the end portions are folded, shown in FIG. 4. The aligned apertures extend through the folded end portions to provide reinforced suture holes 63 and 65 extending through the sheet 52 near opposed ends of the apparatus 50.

In this embodiment, the apparatus 50 also includes an additional sheet 68 of a biocompatible tissue material. The sheet 68 preferably is formed of a cytocompatible material identical to the material forming the other sheet 52, e.g., glutaraldehyde cross-linked pericardium which has been detoxified.

As shown in FIG. 3, the additional sheet 68 is attached to a surface 70 of the sheet 52. The sheet 68 extends longitudinally along an intermediate portion of the sheet 52 located between the apertures 56 and 62. The sheet 68 also has side edges 72 and 74 positioned at respective side edges 76 and 78 of the other sheet 52. The sheets 52 and 68 are connected together, such as by sutures (not shown) or a suitable surgical adhesive. The sheet 68 helps to reduce deformation and folding of the apparatus 50 along its long axis 79 when implanted.

A plurality of apertures 80 are formed through both of the sheets 52 and 58, such as shown in FIGS. 3 and 4. The apertures 80 are substantially identical to the apertures (e.g., 42) shown and described with respect to in FIGS. 1 and 2, although they have longer sidewall portions due to the increased thickness of the apparatus provided by the two sheets 52 and 68.

It will be appreciated that the sheet 68 also could be dimensioned and configured to extend coextensively with the sheet 52. In this way, all the apertures (e.g., 54, 56, 60, 62, 80) extend completely through both sheets. The coextensive layers of such sheets 52 and 68, thus, eliminate the need to fold the end portions as shown in FIG. 4.

Figure 5:
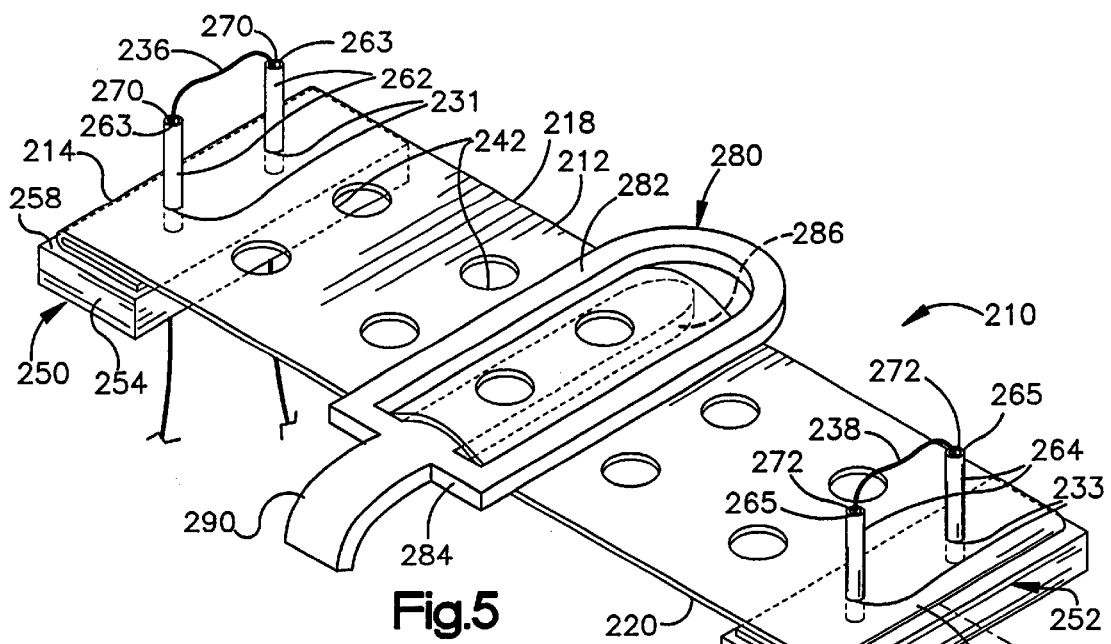
FIG. 5 is an isometric view of a support apparatus in accordance with a fourth embodiment of the present invention.
Figure 6:
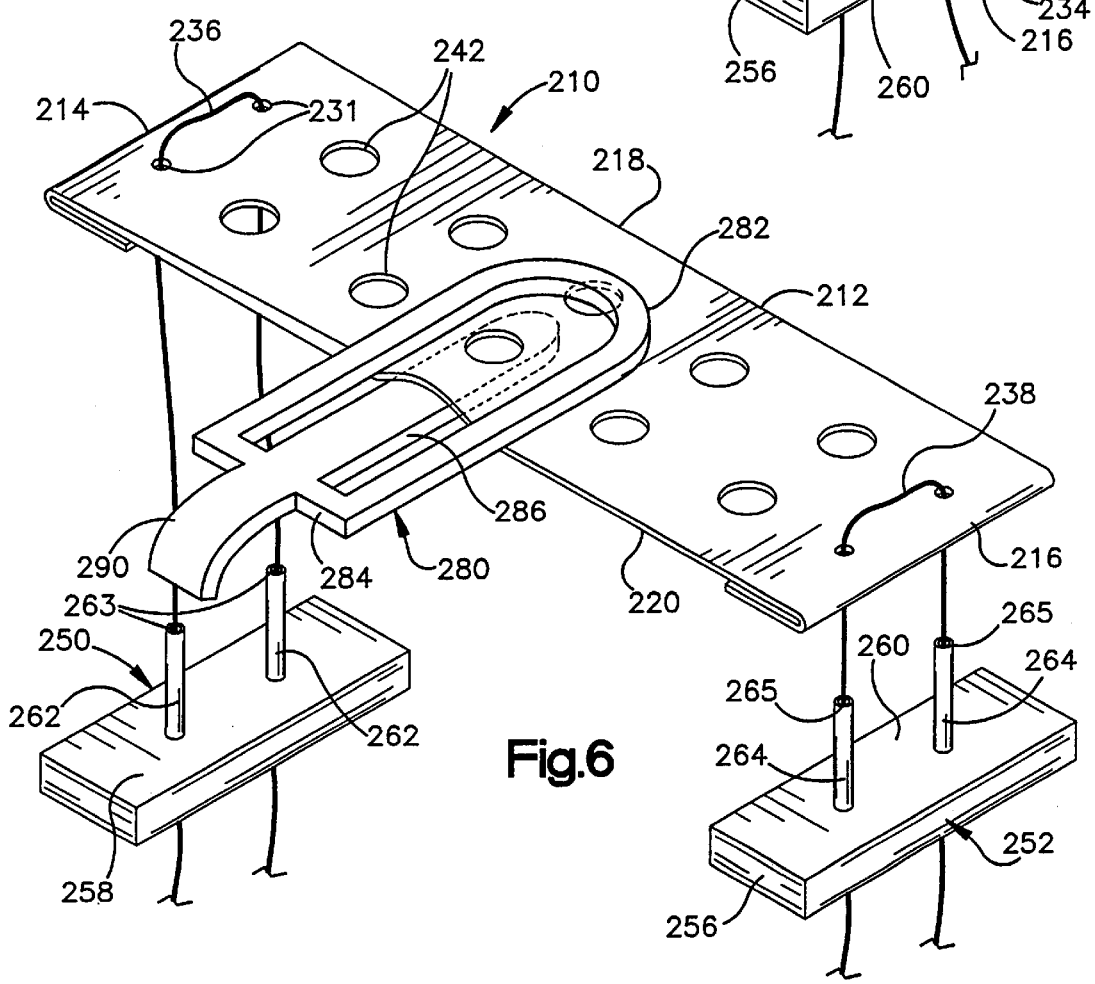
FIG. 6 is another view of the apparatus of FIG. 5 in which part of the apparatus is being removed.

FIGS. 5 and 6 illustrate an apparatus 210 in accordance with yet another embodiment of the present invention. The apparatus includes a sheet 212 of material that is substantially identical to the material 10 shown and described with respect to FIGS. 1 and 2. For simplicity of explanation, identical reference numbers, which have been increased by adding 200, are used in FIGS. 5 and 6 to refer to corresponding parts previously described with respect to FIGS. 1 and 2.

Briefly stated, the sheet 212 is formed of a flexible biocompatible material, such as described above. The sheet 212 has first and second end portions 214 and 216, respectively. The end portions 214 and 216 are spaced apart by a length of the material as defined by side edges 218 and 220. Apertures extend through the sheet near the end portions 214 and 216. In this embodiment, the end portions 214 and 216 are folded transverse to the longitudinal axis 234 of the sheet 212 so that the apertures provide suture holes 231 and 233. The suture holes 231 and 233 extend substantially coaxially through the folded end portions. Alternatively, a pair of apertures may be formed through a single unfolded layer of the sheet 212 near each of the end portions 214 and 216 to provide desired suture holes. The sheet 212 also includes another plurality of apertures 242 that are larger in diameter than the apertures that provide the suture holes 231 and 233.

The apparatus 210 also includes a pair of threading mechanisms 250 and 252. Each threading mechanism 250, 252 has a base portion 254, 256 having a length commensurate with the width of the sheet 212. The threading mechanisms 250 and 252 are removably attachable to the sheet 212 to facilitate threading of sutures 236 and 238 through the respective suture holes 231 and 233. The base 254, 256 of each threading mechanism 250, 252 has a substantially planar surface 258, 260 for engaging a corresponding surface of the sheet 212.

Each threading mechanism 250, 252 further includes a pair of elongated tubular projections 262, 264. The projections 262 and 264 extend outwardly from the surface 258, 260 of the respective threading mechanisms base portions 258 and 260 to terminate in distal ends 263, 265. Each tubular projection 262, 264 includes a substantially cylindrical hollow passage 270, 272 extending longitudinally through each respective projection. The hollow passages 270 and 272 also extend through the associated base portion 254, 256 so that selected sutures may traverse through each passage of the threading mechanisms. The elongated projections 262 and 264 have outer diameters dimensioned according to the size of the respective suture holes 231 and 233. The distal ends 263 and 265 of the tubular projections 262 and 264, respectively, further may be tapered at their distal ends 263 and 265, respectively, to facilitate insertion through the suture holds 231 and 233. In particular, the projections are easily insertable into and through the suture holes 231 and 233. Accordingly, when the threading mechanisms 250 and 252 are attached to the sheet 212, as shown in FIG. 5, the surfaces 258 and 260 engage corresponding folded end portions of the sheet 212.

Once the projections 262 and 264 are inserted through the suture holes 231 and 233, the sutures 236 and 238 are easily inserted through the hollow passages 270 and 272 extending through respective threading mechanisms 250 and 252. The threading mechanisms 250 and 252, thus, permit the sutures 236 and 238 to be threaded with or without the use of needles. The threading mechanisms 250 and 252 help to reduce the occurrence of fraying and weakness at the side edges of the support apparatus 210.

Referring to FIG. 6, once the sutures 236 and 238 have been threaded through the corresponding threading mechanisms 250 and 252 and suture holes 231 and 233, the threading mechanisms are removed from the apparatus 210. The sutures 236 and 238 remain threaded through the suture holes 231 and 233 and the support apparatus 210 may be implanted in a known manner.

Referring back to FIG. 5, another feature of the apparatus 210 is an elongated clip 280 that is removably attached to the sheet 212. In particular, the clip 280 is applied to a portion of the sheet 212 located spaced from and intermediate each of the end portions 214 and 216. The clip 280 extends a length that approximates the width of the sheet 212. When the clip 280 is attached to the sheet 212, it clamps the intermediate portion of the sheet to inhibit folding of a central part of the sheet about its longitudinal axis 234.

By way of example, the clip 280 includes an elongated D-shaped portion 282 that extends from a proximal end 284 of the clip a length at least equal to the width of the sheet 212. The clip 280 also includes another elongated portion 286 that extends from the proximal end 284 a length that also approximates the width of the sheet 212. In the exemplary embodiment of FIGS. 5 and 6, the second elongated portion 286 is slightly shorter than and substantially circumscribed by the first elongated portion 282. The intermediate portion of the sheet 212 is positioned between the elongated portions 282 and 286 so that the clip 280 clamps the intermediate portion of the sheet 212 to inhibit folding of the sheet about its longitudinal axis 234.

The clip 280 also includes a handle 290 that extends from the proximal end 284 in an opposite direction of the elongated clamping portions 282 and 286. The handle 290 may be curved to facilitate gripping. The handle 290 of the clip 280 is grabbed by a surgeon to facilitate removal of the clip 280 from the sheet 212. In order to help inhibit folding of the sheet 212 about the axis 234 when implanted, additional sutures connect the sheet to surrounding tissue of the patient. Such sutures, for example, are applied near the side edges 218 and 220 of the sheet 212 adjacent to each side of the elongated portion 282 of the clip 280. The additional sutures urge the side edges 218 and 220 away from central axis 234 to help inhibit folding of the sheet about its axis after the clip 280 is removed. When the clip 280 and the threading mechanisms 250 and 252 are removed, the apparatus 210 is substantially identical to the apparatus 10 of FIG. 2.

Figure 7:
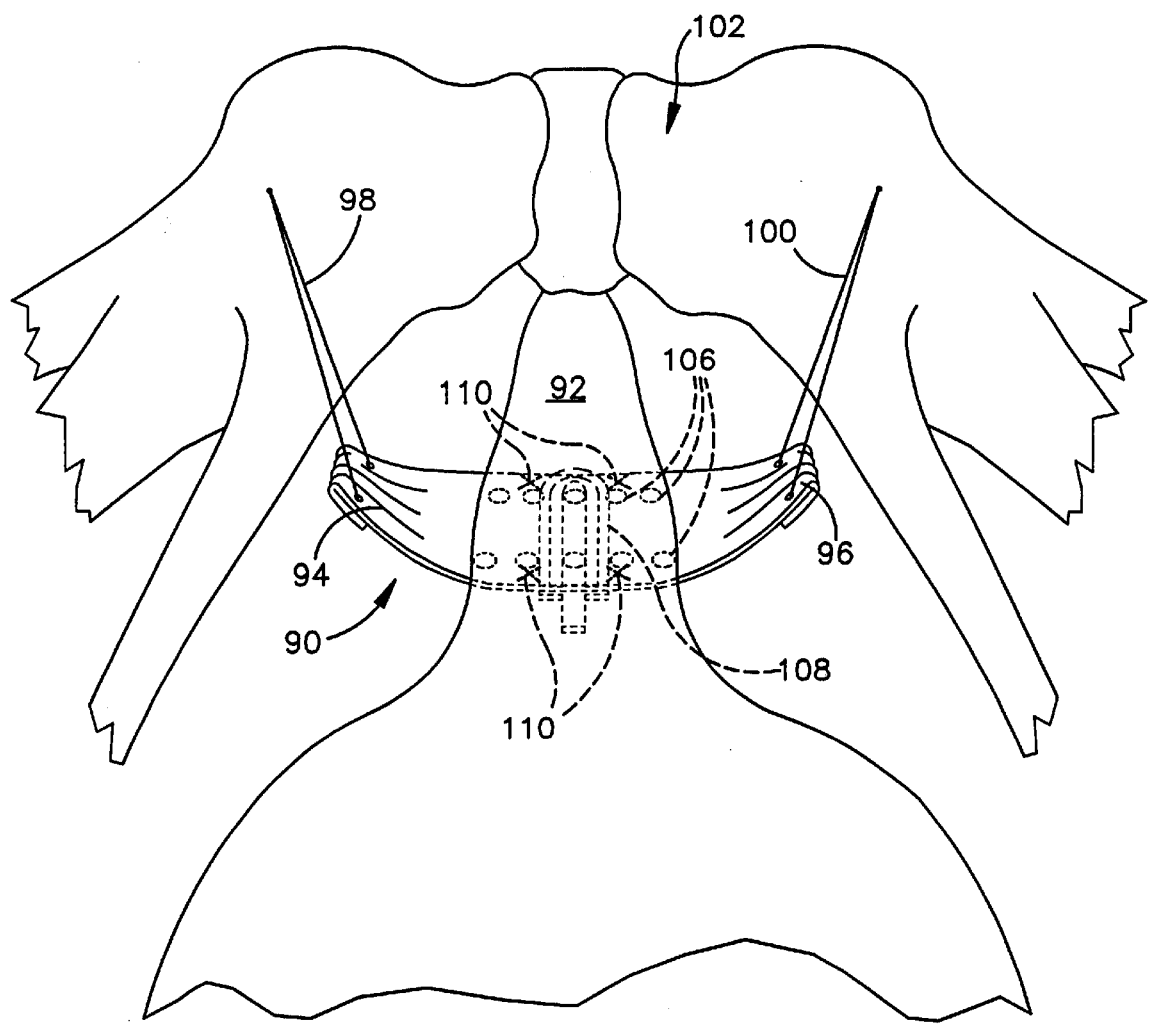
FIG. 7 is a top view of the apparatus of FIG. 5 illustrating an example of its use in accordance with the present invention.

FIG. 7 illustrates an example of an intended use of an implantable support apparatus 90, in accordance with the present invention. Here, the apparatus 90 is used as a suburethral stabilization sling for helping to reduce stress incontinence in women. In particular, the support apparatus 90 is inserted into a passage or tunnel extending through the vaginal mucosa adjacent the urethra 92. The support apparatus 90 is passed through the tunnel so that the intermediate portion located between end portions 94 and 96 thereof is positioned transverse to and supports the urethra 92. The end portions 94 and 96 are folded, as shown in FIGS. 2 and 4–6, to help inhibit fraying or rupturing of the apparatus 90 after being implanted.

Sutures 98 and 100 are inserted through the suture holes formed in the folded end portions 94 and 96 of the apparatus 90, as described above. The sutures 98 and 100 are used to place the apparatus 90 at a desired position relative to the urethra 92. In particular, the sutures 98 and 100 stabilize the end portions 94 and 96 of the support apparatus 90 by being connected to desired tissue of the patient, such as to the pubic bone 102 or to surrounding abdominal muscles.

An example of a vaginal sling procedure is disclosed in the in 1997 instructional materials entitled: *In-Fast Bone Screw System for transvaginal cystourethropexy and vaginal sling procedure, Instructions for use*, which is available from Influence, Inc., of San Francisco, Calif., the content of which instructional material is incorporated herein by reference.

The suture holes formed through the folded end portions 94 and 96 facilitate threading the sutures 98 and 100 through the end portions, shown in FIG. 7. The sutures 98 and 100 may be threaded through the suture holes without the use of a needle. The threading of sutures 98 and 100 preferably is performed using threading mechanisms, as shown and described with respect to FIGS. 5 and 6.

Once connected to desired tissue, the sutures 98 and 100 are tied off so that the support apparatus 90 urges or elevates the urethra toward the posterior surface of a pubic bone to help reduce the effects of urinary stress incontinence. The amount tension needed to properly support the urethra is explored in greater detail in *Use of the Fascial Sling for Neurogenic Incontinence*: Lessons Learned, The Journal of Urology, Vol. 150, 683–386 (1993).

A clip 108, such as shown and described in FIGS. 5 and 6, is used to clamp an intermediate portion of the apparatus 90 to help inhibit folding about its long axis. Once the apparatus 90 is at a desired position and sutures 98 and 108 are appropriately tensioned, additional sutures 110 are applied to attach the apparatus to surrounding tissue. For example, two absorbable sutures 110 are added at each side of the clip 108 to connect an intermediate portion of the apparatus 90 to the adjacent tissue. The clip 108 is then removed. The sutures 110 maintain the desired orientation of the apparatus 90 as well as inhibit its folding, as described above.

The larger apertures 106 formed through the intermediate portion of the apparatus 90 advantageously permit developing scar tissue to embed within and/or pass through the apertures of biocompatible tissue strip. This, together with the sutures 110, helps to straighten the elongated central portion of the apparatus 90 and promote its integration into the surrounding tissue.

Because the tissue is biocompatible, in the absence of such apertures 106, scar tissue would tend to form between the support apparatus 90 and the patient's tissue that is in contact with the apparatus. The formation of scar tissue might cause an implanted biocompatible apparatus (without the apertures 106) to be urged away from the tissue being supported thereby. For the suburethral stabilization procedure, the formation of scar tissue could result in further tightening of the sling apparatus 90, which would cause additional discomfort and/or incontinence to the patient.

The occurrence of longitudinal folds, such as might occur without the clip 108 and sutures 110, causes dead space in which bacteria could collect. As mentioned above, the use of the clip 108 and subsequent sutures 110 helps to inhibit such folding of the apparatus 90 about its longitudinal axis. Consequently, the use of the clip 108 and sutures 110 also helps to reduce the occurrence of infection that might occur as a result of bacteria collecting in the longitudinal folds of the 90 of the apparatus.

Figure 8:
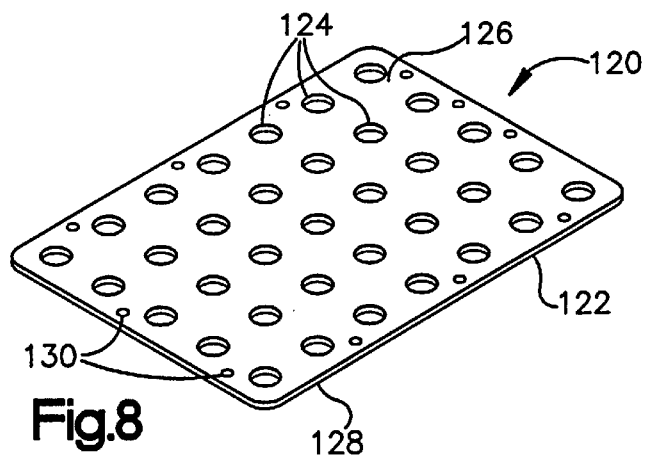
FIG. 8 is an isometric view of a support apparatus in accordance with a third embodiment of the present invention.

FIG. 8 illustrates another embodiment of a support apparatus 120, in accordance with the present invention, which may be used in various surgical applications. The support apparatus 120, for example, may be used to close hernias or support other organs or tissue.

The apparatus 120 is formed of flexible, biocompatible material that is substantially identical to the material shown and described with respect to FIGS. 1–6. The apparatus 120 is formed of a sheet 122 of biological material having a plurality of apertures 124 extending between the opposed surfaces 126 and 128 of the sheet. The apertures 124 typically have diameters ranging from about 2 mm to about 5 mm. The apertures 124 permit scar tissue to grow into and embed therein which improves integration of the apparatus 120 into the patient's body. This provides desired adhesion between the biocompatible tissue material of the apparatus 120 and the patient's surrounding tissue to help hold the sheet 122 at a desired position.

A plurality of suture holes 130 also may be formed through the sheet 122 along the perimeter portion of the sheet. The suture holes 130 facilitate threading sutures through the sheet 122. The suture holes 130 also help inhibit fraying that could otherwise occur along its perimeter portion if, for example, penetrated by a relatively large needle during implantation of the tissue sheet 122.

In view of the foregoing, each of the embodiments shown in FIGS. 1–8 provides an implantable support apparatus with the advantages of cytocompatibility which, when implanted, permits integration and adhesion of the apparatus into surrounding tissue. In particular, apertures are formed through the sheet of tissue material to permit scar tissue to grow into and embed itself within such apertures. This results in improved healing and a lower likelihood of re-operation.

Further, because the apertures at the ends of the apparatus provide suture holes, regardless of whether the end portions are folded (FIGS. 2 and 4–6) or are unfolded (FIGS. 1 and 3), sutures conveniently may be fed through selected apertures without the use of a needle to reduce rupturing and fraying along the end portions of the apparatus. The threading mechanisms further facilitate threading of sutures with or without the use of a needle.

The various apertures may be formed through a respective sheet of the apparatus by cutting or punching holes in a known manner. The apertures may be formed before, during or after treating the tissue so as to render it biocompatible.

From the above description of the invention, those skilled in the art will perceive improvements, changes and modifications. Such improvements, changes and modifications within the skill of the art are intended to be covered by the appended claims.

Having described the invention, the following is claimed:

1. An implantable support apparatus comprising:
   a sheet of a flexible biocompatible material having first and second end portions, a first pair of apertures extend through said sheet near said first end portion and a second pair of apertures extend through said sheet near said second end portion; and
   first and second threading mechanisms, each of said threading mechanisms having a pair of substantially tubular projections insertable into a selected pair of said apertures to facilitate threading of sutures through said first and second pairs of apertures.

2. An apparatus as set forth in claim 1 wherein said apparatus further includes an elongated clip removably attached to said sheet intermediate said end portions of said sheet to inhibit folding of said sheet about an axis extending longitudinally through said end portions of said sheet.

3. An apparatus as set forth in claim 2 wherein said clip has first and second elongated portions extending from an end of said clip, each of said first and second elongated portions engaging opposed sides of said sheet to clamp an intermediate portion of said sheet and inhibit folding of said sheet along the axis.

4. An apparatus as set forth in claim 3 wherein said clip further includes a handle extending from the end of said clip to facilitate removal of said clip from said sheet.

5. An apparatus as set forth in claim 1 wherein each of said threading mechanisms further includes a base portion, said tubular projections extending from a side of said base portion and being spaced apart from each other a distance that approximates the distance between each aperture of said selected pair of apertures.

6. An apparatus as set forth in claim 1 wherein said biocompatible material is a biological tissue material.

7. An apparatus as set forth in claim 6 wherein said biological tissue material is pericardium.

8. An implantable support apparatus comprising:

a sheet of a flexible biocompatible material having first and second end portions and a longitudinal axis extending through said first and second end portions of said sheet, a first pair of apertures extend through said sheet near said first end portion and a second pair of apertures extend through said sheet near said second end portion, a third pair of said apertures extending through said sheet near said first end portion and spaced axially from said first pair of said apertures, a fourth pair of said apertures extending through said sheet near said second end portion and spaced axially from said second pair of said apertures, said first and third pairs of said apertures and said second and fourth pairs of said apertures being arranged so that, upon folding a part of each of said first and second end portions axially toward the opposite end portion, a folded end portion is formed at each end of said sheet in which said first and third pairs of apertures are aligned and said second and fourth pairs of apertures are aligned to provide a reinforced suture holes at each of said folded end portions; and first and second threading mechanisms, each of said threading mechanisms having a pair of substantially tubular projections insertable into a selected pair of said apertures to facilitate threading of sutures through said first and second pairs of apertures.

9. An implantable support apparatus comprising:

a sheet of a flexible biocompatible material having first and second end portions, a first pair of apertures extend through said sheet near said first end portion and a second pair of apertures extend through said sheet near said second end portion each of said first and second pairs of apertures has a first diameter, the biocompatible material comprising a biological tissue material;

another plurality of apertures extending through said sheet at locations spaced from and intermediate said first and second pairs of apertures, each of said another plurality of apertures having a second diameter that is greater than the first diameter so that, when said apparatus is implanted, surrounding tissue embeds into said another plurality second apertures to facilitate integration of said apparatus into the surrounding tissue; and first and second threading mechanisms, each of said threading mechanisms having a pair of substantially tubular projections insertable into a selected pair of said apertures to facilitate threading of sutures through said first and second pairs of apertures.

10. An apparatus as set forth in claim 1, each of the tubular projections further comprising hollow passages that extend longitudinally therethrough, at least one length of suture extending through the hollow passages of the tubular projections.

* * * * *

UNITED STATES PATENT AND TRADEMARK OFFICE
CERTIFICATE OF CORRECTION

PATENT NO. : 6,599,318 B1
DATED : July 29, 2003
INVENTOR(S) : Shlomo Gabbay

It is certified that error appears in the above-identified patent and that said Letters Patent is hereby corrected as shown below:

<u>Column 10,</u>
Line 27, insert:
-- 11. A method for using the apparatus of claim 1, comprising; inserting the tubular projections of the first and second threading mechanisms into respective first and second pairs of apertures of the sheet; inserting sutures through hollow passages of the tubular projections;
removing the tubular projections so that the sutures remain in the respective apertures at the end portions and connecting the sheet to desired tissue using the sutures --.

Signed and Sealed this

Twenty-seventh Day of July, 2004

JON W. DUDAS
*Acting Director of the United States Patent and Trademark Office*